United States Patent
Muthukumaran et al.

(10) Patent No.: US 7,982,032 B2
(45) Date of Patent: Jul. 19, 2011

(54) PROCESS FOR THE PREPARATION OF 10,11-DIHYDRO-10-OXO-5H-DIBENZ[B, F]AZEPINE-5-CARBOXAMIDE

(75) Inventors: Mandakini Muthukumaran, Baroda (IN); Muthukumaran Natarajan, Baroda (IN); Rajamannar Thennati, Baroda (IN)

(73) Assignee: Sun Pharmaceutical Industries Limited, Andheri (E), Mumbai (IN)

( * ) Notice: Subject to any disclaimer, the term of this patent is extended or adjusted under 35 U.S.C. 154(b) by 744 days.

(21) Appl. No.: 10/598,623

(22) PCT Filed: Mar. 10, 2005

(86) PCT No.: PCT/IN2005/000077
§ 371 (c)(1),
(2), (4) Date: May 5, 2008

(87) PCT Pub. No.: WO2005/096709
PCT Pub. Date: Oct. 20, 2005

(65) Prior Publication Data
US 2008/0269480 A1    Oct. 30, 2008

(30) Foreign Application Priority Data
Mar. 11, 2004  (IN) .......................... 304/MUM/2004

(51) Int. Cl.
*C07D 223/22*  (2006.01)
*C07D 223/28*  (2006.01)
(52) U.S. Cl. ........................ 540/589; 540/591
(58) Field of Classification Search ............... 540/589, 540/591
See application file for complete search history.

(56) References Cited

U.S. PATENT DOCUMENTS
5,808,058 A  *  9/1998  Milanese .................. 540/588
* cited by examiner

*Primary Examiner* — Brenda Coleman
(74) *Attorney, Agent, or Firm* — Pharmaceutical Patent Attorneys, LLC

(57) ABSTRACT

A process for preparing 10,11-dihydro-10-oxo-5H-dibenz[b, f]azepine-5-carboxamide, compound of formula (I), said process comprising a. reacting compound of formula (Ivb) with alkali metal methoxide to yield compound of formula (II); and b. converting compound of formula (II) to compound of formula (I).

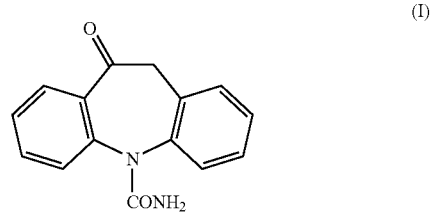

(I)

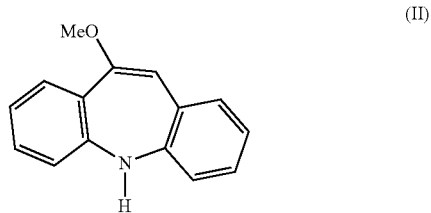

(II)

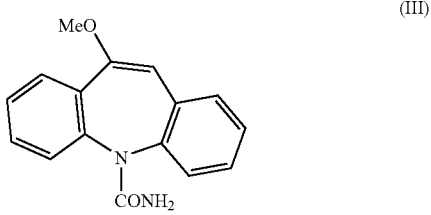

(III)

12 Claims, No Drawings

PROCESS FOR THE PREPARATION OF 10,11-DIHYDRO-10-OXO-5H-DIBENZ[B,F]AZEPINE-5-CARBOXAMIDE

RELATED APPLICATIONS

This application is a National Stage Entry of PCT Application No. PCT/IN2005/000077, filed on 10 Mar. 2005, which in turn claims priority from Indian Priority Application No. 304/MUM/2004, filed on 11 Mar. 2004.

The present invention relates to a process for the preparation of 10,11-dihydro-10-oxo-5H-dibenz[b,f]azepine-5-carboxamide, compound of formula I, commonly known as oxcarbazepine (INN Name) used in therapy as an anticonvulsant.

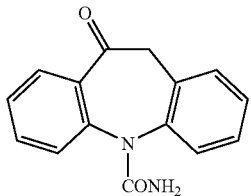

Formula I

BACKGROUND OF THE INVENTION

U.S. Pat. No. 3,642,775 (Assigned to: Ciba Giegy Corporation) describes the preparation of compound of formula I from compound of formula II.

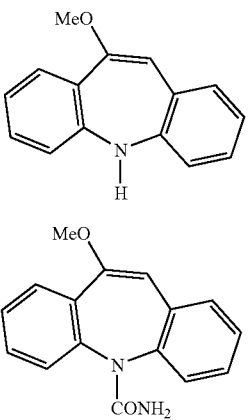

Formula II

Formula III

The compound of formula II is reacted with phosgene in toluene and subsequently with ammoniacal ethanol to yield compound of formula III. Hydrolysis of compound of formula III with dilute mineral acid gives the desired product, compound of formula I.

U.S. Pat. No. 5,808,058 (Assigned to M/s Trifarma) describes a different method for the synthesis of compound of formula I. Compound of formula II is subjected to direct carbamoylation with isocyanic acid generated in situ from cyanate and acid to generate compound of formula III which on acid hydrolysis furnishes the desired product.

Different routes for the preparation of compound of formula I are suggested in prior art starting from compound of formula II. The compound of formula II is an essential intermediate for preparing compound of formula I.

GB patent specification 943,277 describes the process for the preparation of compound of formula II, intermediate for preparing compound of formula I from compound of formula IVa.

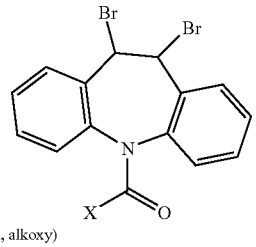

Formula IVa (X = lower alkyl, alkoxy)

The process exemplified in this patent discloses treating compound of formula IVa (X=CH$_3$) with alkali metal hydroxide to yield monobromoazepine, compound of formula V after 14 hours at room temperature.

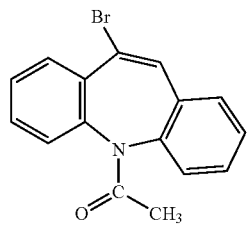

Formula V

The compound of formula V is then refluxed with excess alkali metal alkanoate for 18 hours to result in compound of formula II. Also disclosed is direct conversion of compound of formula IVa to compound of formula II in about 32-40 hours. The process of the present invention uses a different starting material to prepare compound of formula II in shorter reaction times.

We have now developed a novel process for preparation of 10,11-dihydro-10-oxo-5H-dibenz[b,f]azepine-5-carboxamide, compound of formula I, in substantially pure form starting with compound of formula IVb.

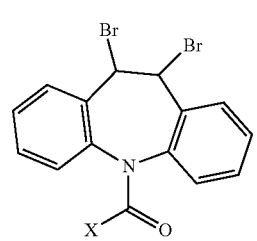

Formula IVb (X = Cl, Br)

The process of the present invention is advantageous as it prepares compound of formula II from compound of formula IVb in shorter reaction times. The compound of formula II is then converted to compound of formula I.

OBJECT OF THE INVENTION

The object of the present invention is to provide a novel process for the preparation of compound of formula I.

Another object of the present invention is to prepare compound of formula I and formula VI which are intermediates used in the preparation of compound of formula I by novel process in shorter reaction times.

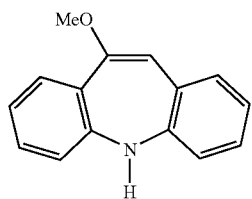

Formula II

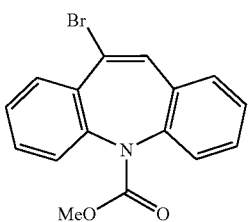

Formula VI

SUMMARY OF THE INVENTION

The present invention provides a process for preparation of 10,11-dihydro-10-oxo-5H-dibenz[b,f]azepine-5-carboxamide, compound of formula I, said process comprising

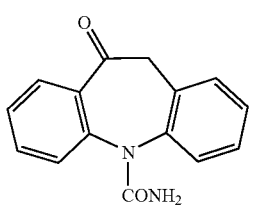

Formula I (a) reacting compound of formula IVb with alkali metal methoxide to yield compound of formula II; and

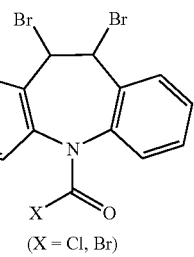

Formula IVb

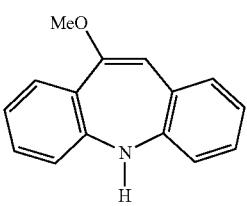

Formula II (b) converting compound of formula II to compound of formula I.

The present invention also provides a process for preparing 10,11-dihydro-10-oxo-5H-dibenz[b,f]azepine-5-carboxamide, compound of formula I,

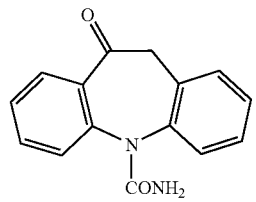

Formula I said process comprising (a) dehydrobrominating and esterifying compound of formula IVb to give compound of formula VI; and

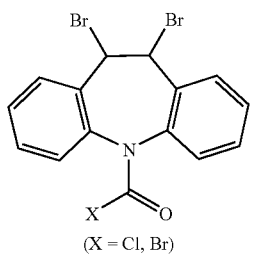

Formula IVb

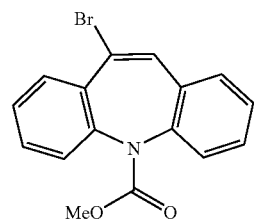

Formula VI (b) converting compound of formula VI to compound of formula I.

DETAILED DESCRIPTION OF THE INVENTION

We have now developed a novel process for the preparation of 10,11-dihydro-10-oxo-5H-dibenz[b,f]azepine-5-carboxamide, compound of formula I, starting from compound of formula IVb.

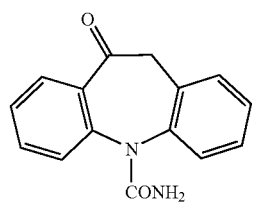

Formula I

-continued

Formula IVb

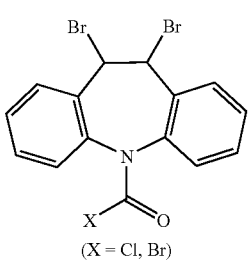

(X = Cl, Br)

The compound of formula IVb is used to prepare compounds of formula II and VI, intermediates for preparing compound of formula I.

Formula II

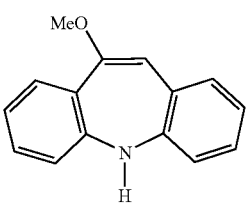

Formula VI

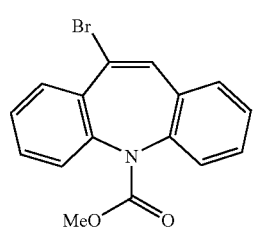

According to the process of the present invention compound of formula II and VI may be prepared by reacting compound of formula IVb with alkali metal methoxide under different reaction conditions.

According to one embodiment of the process of the present invention compound of formula IVb on reaction with alkali metal methoxide in the molar ratio of about 1:12 to 1:15 directly yields the compound of formula II in one pot.

The alkali metal methoxide may be selected from sodium methoxide, potassium methoxide and the like. The reaction may be carried out by heating to about 30-120° C. preferably about 50-100° C. The reaction with alkali metal methoxide may be carried out for about 16 to 20 hours.

According to another embodiment of the process of the present invention compound of formula IVb is dehydrobrominated and esterified with alkali metal methoxide to give compound of formula VI.

Formula VI

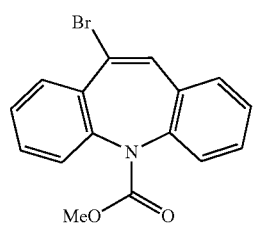

The molar ratio of compound of formula IVb to alkali metal methoxide for dehydrobromination and esterification is about 1:2 to 1:3.

The alkali metal methoxide for dehydrobromination and esterification may be selected from sodium methoxide, potassium methoxide and the like. The dehydrobromination and esterification may be carried out by heating to about 40-70° C. preferably about 50-60° C. The dehydrobromination and esterification reaction may be carried out for about 2 to 5 hours.

The compound of formula VI obtained by following the process of the present invention on reaction with alkali metal methoxide in the molar ratio of about 1:12 to 1:15 yields compound of formula II. The alkali metal methoxide may be selected from sodium methoxide, potassium methoxide and the like. The reaction may be carried out by heating to about 70-100° C. preferably about 80-90° C. The reaction may be carried out for about 12 to 18 hours.

The compound of formula II obtained by following the process of the present invention is then converted to compound of formula I using any process known to a person skilled in the art such as U.S. Pat. No. 5,808,058.

The compound of formula I thus obtained may be further purified by recrystallization from solvent(s) to yield ICH grade material (purity not less than 99%). The solvent(s) may be selected from polar aprotic solvent, hydrocarbon solvent and their mixtures. When mixture of polar aprotic solvent and hydrocarbon solvent is used the volume ratio may vary from 1:0.5 to 1:5. Optionally second recrystallization may be carried out from aqueous acidic solutions such as dilute acetic acid.

The starting material compound of formula IVb may be prepared by any prior known method such as brominating compound of formula VII, with bromine in acetic acid.

Formula VII

The invention is further illustrated but not restricted by the description in the following examples.

EXAMPLES

Example 1

(a) Preparation of 10,11-Dibromo-10,11-dihydrodibenzo[b,f]azepine-5-carbonylchloride, compound of formula IVb 1 Kg of Dibenzo[b,f]azepine-5-carbonylchloride is added to 5.0 L acetic acid and the mixture stirred for 5 minutes to get uniform slurry. 273 ml of liquid bromine is added dropwise by maintaining the batch temperature at 30-35° C. over a period of 1-2 hours. The reaction mixture is stirred for 1-2 hours at 32-35° C. followed by cooling to 15-20° C. The reaction mixture is quenched by adding aqueous sodium thiosulfate solution. Cool the contents, filter and wash with water and dry to yield compound of formula IVb.

(b) Preparation of Methyl-10-bromo-dibenz[b,f]azepine-5-carbamate, compound of formula VI 1.037 kg of sodium methoxide solution is added to 1 liter of methanol. The mixture is cooled to 30-35° C. and 1 kg of 10,11-Dibromo-10,11-dihydrodibenzo[b,f]azepine-5-carbonylchloride, compound of formula IVb, is added in lots under stirring by maintaining the temperature between 50-55° C. The suspension is stirred at 50-55° C. for 45 minutes to 1 hour. The reaction mixture is cooled. The product is filtered and washed with water and dried to obtain compound of formula VI.

(c) Preparation of 10-Methoxy-dibenz[b,f]azepine, compound of formula II from compound of formula VI 0.25 kg of Methyl-10-bromo-dibenz[b,f]azepine-5-carbamate, compound of formula VI, is added to 1.962 kg of 25% sodium methoxide solution under stirring at room temperature. The reaction mixture is heated to 88-93° C. and stirred at that temperature for 12-16 hours. The reaction mixture is cooled. The product is filtered and washed with water and dried. The product obtained is further purified by using toluene:DMF (15 volumes:1 volume) mixture to furnish compound of formula II.

Example 2

Preparation of 10-Methoxy-dibenz[b,f]azepine, compound of formula II from compound of formula IVb 1.037 kg of sodium methoxide solution is added to 1 liter of methanol. The mixture is cooled to 30-35° C. and 1 kg of 10,11-Dibromo-10,11-dihydrodibenzo[b,f]azepine-5-carbonylchloride, compound of formula IVb, is added in lots under stirring by maintaining the temperature between 50-55° C. The suspension is stirred at 50-55° C. for 45 minutes to 1 hour. The reaction mixture is cooled to 30-40° C. & 6 kg of 25% sodium methoxide solution is added to the reaction mixture under stirring at room temperature. The reaction mixture is heated to 88-93° C. and stirred at that temperature for 12-16 hours. The reaction mixture is cooled. The product is filtered and washed with water and isopropanol to get compound of formula II.

Example 3

Preparation of 10,11-dihydro-10-oxo-5H-dibenz[b,f]azepine-5-carboxamide, compound of formula I 25 g of 10-Methoxy-dibenz[b,f]azepine, compound of formula II, (from example 1 or 2) is mixed with 10 g sodium cyanate. The mixture is added in parts to 200 ml acetic acid at 25-30° C. over a period of 20-30 minutes by maintaining the temperature between 33-35° C. The reaction mixture is allowed to stir at 33-35° C. for 1 hour. 24 ml of concentrated sulfuric acid solution is added slowly to the reaction mixture by maintaining the temperature between 33-35° C. and stirred for 1-2 hours. The reaction mixture is quenched slowly by adding acetone and charcoalized. Filter and cool the filtrate. Charge water to the filtrate and cool the product slurry. Filter the product and wash with water till the filtrate is neutral to pH paper. The product obtained is further purified by using toluene methanol mixture (1:1) volume parts to get crude compound of formula I. To crude product add DMF. Heat the contents gradually to 95-100° C. under stirring. Stir for 1 hour at 95-100° C. Charge slowly toluene by maintaining the temperature between 95-100° C. Stir for 1.0 hour at 3-6° C. Filter the product at 3-6° C. and wash with toluene to get compound of formula 1, with HPLC purity of 99.87%.

We claim:
1. A process for preparing 10,11-dihydro-10-oxo-5H-dibenz[b,f]azepine-5-carboxamide, compound of formula I,

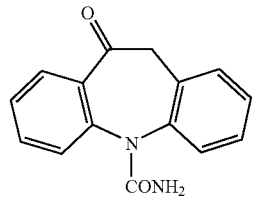

Formula I said process comprising
(a) reacting compound of formula IVb with alkali metal methoxide to yield compound of formula II; and

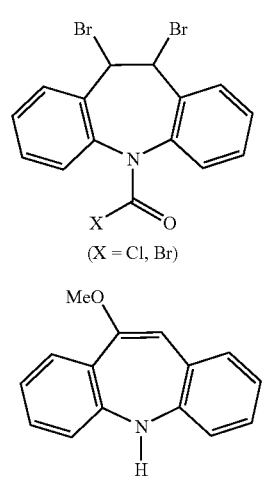

Formula IVb (X = Cl, Br)

Formula II (b) converting compound of formula II to compound of formula I.

2. A Process as claimed in claim 1 wherein in step (a) the alkali metal methoxide is selected from sodium methoxide and potassium methoxide.

3. A process as claimed in claim 1 wherein in step (a) the molar ratio of compound of formula IVb to alkali metal methoxide is about 1:12 to 1:15.

4. A process as claimed in claim 1 wherein step (a) is carried out for about 16 to 20 hours.

5. A process for preparing 10,11-dihydro-10-oxo-5H-dibenz [b,f]azepine-5-carboxamide, compound of formula I,

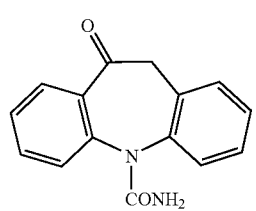

Formula I said process comprising
(a) dehydrobrominating and esterifying compound of formula IVb to give compound of formula VI; and

Formula IVb

[structure: 10,11-dibromo-dibenzazepine with N-C(=O)-X, X = Cl, Br]

Formula VI

[structure: 10-bromo-dibenzazepine with N-C(=O)-OMe]

(b) converting compound of formula VI to compound of formula I.

6. A process as claimed in claim 5 wherein step (a) is carried out with alkali metal methoxide.

7. A process as claimed in claim 6 wherein alkali metal methoxide is selected from sodium methoxide and potassium methoxide.

8. A process as claimed in claim 6 wherein the molar ratio of compound of formula IVb to alkali metal methoxide is about 1:2 to 1:3.

9. A process as claimed in claim 5 where in step (a) is carried out for about 2 to 5 hours.

10. A process for preparing compound of formula II, said process comprising reacting compound of formula IVb with alkali metal methoxide to yield compound of formula II

Formula IVb

[structure: 10,11-dibromo-dibenzazepine with N-C(=O)-X, X = Cl, Br]

Formula II

[structure: 10-methoxy-dibenzazepine with N-H]

11. A process for preparing compound of formula VI, said process comprising dehydrobrominating and esterifying compound of formula IVb to give compound of formula VI

Formula IVb

[structure: 10,11-dibromo-dibenzazepine with N-C(=O)-X, X = Cl, Br]

Formula VI

[structure: 10-bromo-dibenzazepine with N-C(=O)-OMe]

12. A process as claimed in claim 11 wherein dehydrobromination and esterification is carried out with alkali metal methoxide.

\* \* \* \* \*